US011541031B2

(12) United States Patent
Blanchard et al.

(10) Patent No.: US 11,541,031 B2
(45) Date of Patent: Jan. 3, 2023

(54) COCOA POLYPHENOLS AND SOLUBLE DIETARY FIBER FOR USE IN THE TREATMENT OR PREVENTION DISORDERS ASSOCIATED WITH AN ABOVE-NORMAL NUMBER OF GRANULOCYTES IN A TISSUE

(71) Applicant: NESTEC S.A., Vevey (CH)

(72) Inventors: Carine Blanchard, Le Mont-sur-Lausanne (CH); Sebastien Holvoet, Oron la Ville (CH); Rinat Ran-Ressler, Minnetonka, MN (US); Martinas Kuslys, Grosshoechstetten (CH)

(73) Assignee: Societe des Produits Nestle S.A., Vevey (CH)

( * ) Notice: Subject to any disclaimer, the term of this patent is extended or adjusted under 35 U.S.C. 154(b) by 692 days.

(21) Appl. No.: 15/780,490

(22) PCT Filed: Dec. 1, 2016

(86) PCT No.: PCT/EP2016/079423
§ 371 (c)(1),
(2) Date: May 31, 2018

(87) PCT Pub. No.: WO2017/093397
PCT Pub. Date: Jun. 8, 2017

(65) Prior Publication Data
US 2019/0008824 A1 Jan. 10, 2019

Related U.S. Application Data

(60) Provisional application No. 62/262,990, filed on Dec. 4, 2015.

(51) Int. Cl.
| | | |
|---|---|---|
| *A61K 31/353* | (2006.01) | |
| *A61K 31/05* | (2006.01) | |
| *A23L 33/105* | (2016.01) | |
| *A23L 33/21* | (2016.01) | |
| *A61P 37/08* | (2006.01) | |
| *A61P 1/00* | (2006.01) | |
| *A61K 36/185* | (2006.01) | |
| *A61K 47/14* | (2017.01) | |
| *A61K 47/36* | (2006.01) | |
| *A61K 9/00* | (2006.01) | |

(52) U.S. Cl.
CPC .......... *A61K 31/353* (2013.01); *A23L 33/105* (2016.08); *A23L 33/21* (2016.08); *A61K 31/05* (2013.01); *A61K 36/185* (2013.01); *A61K 47/14* (2013.01); *A61K 47/36* (2013.01); *A61P 1/00* (2018.01); *A61P 37/08* (2018.01); *A23V 2002/00* (2013.01); *A23V 2200/304* (2013.01); *A23V 2200/32* (2013.01); *A23V 2250/2132* (2013.01); *A23V 2250/5072* (2013.01); *A61K 9/006* (2013.01)

(58) Field of Classification Search
None
See application file for complete search history.

(56) References Cited

U.S. PATENT DOCUMENTS

| | | | |
|---|---|---|---|
| 8,691,213 B2 * | 4/2014 | Langford | ............. A23L 33/25 424/93.4 |
| 10,350,252 B2 * | 7/2019 | Blanchard | ............. A23L 33/105 |
| 2006/0094688 A1 | 5/2006 | Tanaka et al. | |
| 2015/0196610 A1 | 7/2015 | Madhavamenon et al. | |

FOREIGN PATENT DOCUMENTS

| | | |
|---|---|---|
| CN | 101011082 A | 8/2007 |
| CN | 101715965 A | 6/2010 |
| CN | 103462041 A | 12/2013 |
| JP | 2014511871 A | 5/2014 |
| JP | 2014529603 A | 11/2014 |
| WO | 2015040223 A1 | 3/2015 |

OTHER PUBLICATIONS

Prussian (Gastroenterol Clin North Am (Jun. 2014), vol. 43, No. 2, pp. 317-327).*
Massot-Cladera et al. "Impact of cocoa polyphenol extracts on the immune system and microbiota in two strains of young rats" British Journal of Nutrition, 2014, vol. 112, pp. 1944-1954.
Perez-Cano et al. "The effects of cocoa on the immune system" Frontiers in Pharmacology, Jun. 2013, vol. 4, article 71, 12 pages.
Abril-Gil et al. "A diet enriched with cocoa prevents IgE synthesis in a rat allergy model" Pharmacological Research, 2012, vol. 65, pp. 603-608.
Massot-Cladera et al. "Cocoa modulatory effect on rat faecal microbiota and colonic crosstalk" Archives of Biochemistry and Biophysics, 2012, vol. 527, pp. 105-112.
Trompette et al., "Gut Microbiota Metabolism of Dietary Fiber Influences Allergic Airway Disease and Hematopoiesis", Nature Medicine, Jan. 5, 2014, pp. 1-10.
China Patent Office Communication for Application No. 201680067186. X, dated Feb. 2, 2021, 14 pages.
Japan Patent Office Communication for Application No. P2018-526233, Dispatch No. 606715, dated Aug. 3, 2021, 8 pages.

* cited by examiner

*Primary Examiner* — Susan Hoffman
(74) *Attorney, Agent, or Firm* — K&L Gates LLP (57) ABSTRACT

The present invention relates to a composition comprising at least one cocoa polyphenol and soluble dietary fiber for use in the prevention or treatment of a disorder associated with an above-normal number of granulocytes in a tissue.

23 Claims, 1 Drawing Sheet

COCOA POLYPHENOLS AND SOLUBLE DIETARY FIBER FOR USE IN THE TREATMENT OR PREVENTION DISORDERS ASSOCIATED WITH AN ABOVE-NORMAL NUMBER OF GRANULOCYTES IN A TISSUE

CROSS REFERENCE TO RELATED APPLICATIONS

The present application is a National Stage of International Application No. PCT/EP2016/079423, filed on Dec. 1, 2016, which claims priority to U.S. Provisional Patent Application No. 62/262,990, filed on Dec. 4, 2015, the entire contents of which are being incorporated herein by reference.

FIELD OF INVENTION

The present invention relates to compositions comprising cocoa polyphenols and dietary fiber for use in the treatment or prevention of disorders associated with an above-normal number of granulocytes in a tissue, in particular, a eosinophilic gastrointestinal disorder, food allergy, allergy associated with aeroallergens, and related disorders.

BACKGROUND

An increased number of granulocytes, such as eosinophils or mast cells, in a tissue is associated with a number of disorders, like various, gastrointestinal disorders, food allergies, and atopic dermatitis.

For example, eosinophilic esophagitis is an inflammatory condition of the esophagus that can be triggered or not by an antigen. Symptoms include functional abdominal pain, vomiting, difficultly to thrive, swallowing difficulty, food impaction, and heartburn. The disease was initially described in children but occurs in adults as well. Eosinophils can usually not be found in normal esophageal mucosa. However, in eosinophilic esophagitis the eosinophils infiltrate the epithelium of the esophagus and can often be found in clusters close to the surface of the epithelium. Frequently the infiltration of the eosinophils is associated with a thickening of the basal layer as a reaction to the inflammatory activities in the epithelium. Mast cells are granulocytes that are also increased in eosinophilic gastrointestinal disorders and are part of the pathogenesis.

There are different strategies available for the treatment of disorders associated with an above-normal number of granulocytes in a tissue including medical therapy, mechanical dilatation, and modification of the diet.

In medical therapy corticosteroids and proton pump inhibitors have been found to mitigate the symptoms granulocyte infiltration. It has also been observed that the allergic response can be reduced by the administration of antihistamines. Mechanical dilatation of the esophagus might be considered in severe cases where the swelling of the epithelium is threatening to block the esophagus.

Previous nutritional treatment regimens mainly aim at elimination of the allergen (or causative foods) from the diet. Dietary modification often leads to use of hypoallergenic protein compositions like compositions only comprising free amino acids or extensively hydrolyzed protein. For example, US 2008/0031814 describes a nutritional composition lacking allergenic ingredients and thereby preventing the development of allergic inflammatory conditions. Thus, instead of treating the disease by the choice of certain nutritional ingredients the diets of the prior art aim at avoiding allergenic ingredients in the diet.

Therefore, there is a need for a composition comprising natural compounds that does not only lacks main allergens but can actively prevent or treat food induced gastrointestinal inflammatory diseases such as eosinophilic gastrointestinal disorders (EGID). EGID include Eosinophilic esophagitis, eosinophilic gastritis, eosinophilic enthero-colitis and eosinophilic colitis.

SUMMARY

It is the object of the invention to provide new and alternative solutions to the problem of preventing or treating disorders associated with an above-normal number of granulocytes in a tissue.

It has been surprisingly found that a combination of cocoa polyphenols with soluble dietary fiber is useful in preventing or treating disorders associated with an above-normal number of eosinophils and mast cells in a tissue. The evaluation of ingredients which are useful in the treatment or prevention of eosinophilic esophagitis is performed using an established mouse model for eosinophilic esophagitis (Akei et al., "Epicutaneous antigen exposure primes for experimental eosinophilic esophagitis in mice", Gastroenterology, 2005 September; 129(3):985-94). This model uses various parameters including the number of eosinophils in the esophagus as indicators for the effect on eosinophilic esophagitis or number of mast cells in the gastrointestinal track for allergic gastrointestinal intestinal inflammation such as EGID. Accordingly, this model is ideally suited for the testing of compounds that are candidates for the treatment or prevention of allergic gastrointestinal inflammation such as eosinophilic gastro-intestinal disorders.

DEFINITIONS

"Eosinophilic Gastrointestinal Disorders (EGIDs) is a chronic and complex group of diseases which can affect adults and children. These disorders are characterized by having above normal amounts of eosinophils and mast cells, types of white blood cell, in one or more specific places anywhere in the digestive system. Mast cells are effector cells of allergic inflammation as directly responsible of histamine degranulation in case of allergic reaction. EGID is further subdivided into organ-specific diagnosis. For example, Eosinophilic Gastritis means eosinophils infiltrating the stomach. While visual inflammation is not always present, inflammation may be apparent under the microscope. EGIDS in the sense of the invention can be eosinophilic esophagitis, eosinophilic gastritis, eosinophilic gastroenteritis, or eosinophilic colitis.

"Granulocytes" in this application includes but are not restricted to eosinophils and mast cells. Eosinophils are marker of EGIDS as increased number is found in the disease state. Mast cells are also increased in disease state but are rather effector cells of allergic inflammation as directly responsible of histamine degranulation in case of allergic reaction.

"Eosinophilic esophagitis" is an inflammatory condition of the esophagus. Symptoms include functional abdominal pain, vomiting, difficultly to thrive, swallowing difficulty, food impaction, acid reflux and heartburn. It is characterized by the presence of eosinophilic and mast cells infiltrates in the epithelium of the esophagus. The infiltration of the eosinophils can be associated with a thickening of the basal layer. Under the ICD-9 (international classification of diseases revision 9) it is designated as 530.13. If more than 15 eosinophils per "high power field" (defined below) are found in a mucosal biopsy of the esophagus the disease eosinophilic esophagitis can be considered as diagnosed.

"Food allergy" is an adverse immune response to certain kinds of food. Food allergies are different from food intolerance, pharmacological reactions, and toxin-mediated reactions. The most common allergic component is the protein in the food. These kinds of allergies occur when the body's immune system mistakenly identifies a protein as harmful. The immune system, thinking the organism (the individual) is being invaded, sends white blood cells to attack, and that triggers an allergic reaction. These reactions can range from mild to severe. Allergic responses include dermatitis, gastrointestinal (e.g. EGIDs) and respiratory distress.

"Plant phenols" are a class of natural organic compounds. They comprise one or more phenolic groups. Only phenols that occur in plants and artificially synthesized phenols that are identical to phenols naturally occurring in plants are considered here.

"Phenolic groups" are groups that comprise a phenyl group bonded to a hydroxyl group. The hydrogen of the ring carbons of the phenolic groups can be substituted with further residues (like hydroxyl-, alkan-, alken-residues, ring C formed as carboxyl etc.). A particular preferred substitution is a further hydroxyl group.

"Plant polyphenols" in the sense of the invention are phenols comprising more than 2 phenolic groups.

"Procyanidin" is a form of a polyphenol. Polyphenols consist of more than one aromatic ring with each containing at least one hydroxyl group. Flavonoids are a subclass of polyphenols that have a C6-C3-C6 backbone structure. One group of flavonoids, the procyanidins, are composed of flavan-3-ol monomers and their respective oligomers, commonly bonded through a 4→6 or 4→8 linkage. Multimeric forms of said procyanidin do also naturally occur. For a definition of procyanidins in the sense of the invention we refer to Hammerstone, John F.; Lazarus, Sheryl A.; Schmitz, Harold H. (August 2000; "Procyanidin content and variation in some commonly consumed foods". The Journal of nutrition 130 (8S Suppl): 2086S-92S. PMID 10917927), in particular the introduction.

"High Power Field (HPF)" when used in relation to the invention refers to the area visible under the maximum magnification power of the objective of a microscope being used. This can represent a 400× magnification level.

"Topic-oral" when used in this invention is a form of administration where a composition is applied topically to an accessible mucosa, in particular, the esophageal mucosa for direct adsorption of the composition by the respective mucosa. This form of administration is intended to avoid adsorption of the composition via the digestive tract starting after the esophagus. A typical form of topical-oral administration is the administration in form of spray that is sprayed via the oral cavity and then swallowed into the esophagus.

"Amino acids in free form" are amino acids that are comprised in a composition as free amino acids, and are thus not contained in peptides or proteins.

Hence, "amino acids in bound form" are amino acids being part of peptides, proteins, or covalently bound to other compounds.

"Protein amino acids" are those amino acids that are found in naturally produced proteins, including those that are used by the translation machinery to produce proteins and those that that are modified in proteins subsequently to translation.

"Non-protein amino acids" are those amino acids that are not found in naturally produced proteins but which are metabolites or structural components in cells and organisms.

The term "degree of hydrolysis" refers to the extent to which peptide bonds are broken by a hydrolysis method. The peptides present after hydrolysation may be hydrolyzed to various extent.

The term "partially hydrolyzed" means having a degree of hydrolysis which is greater than 0% but less than 50%.

The term "extensively hydrolyzed" means having a degree of hydrolysis which is greater than or equal to 50%.

The present invention contemplates partially and extensively hydrolyzed proteins.

Above normal numbers of eosinophils can be observed in the mucosa of the esophagus, of the stomach, or the colon, or can be observed in the skin. Thus, above normal numbers of eosinophils can be observed in any tissues that are exposed to foreign antigens, i.e. antigens that are not found in the individual harboring the tissues.

Each tissue of a healthy individual will have a characteristic number of eosinophils or mast cells which can also be zero. This number of granulocytes can be raised due to eosinophilic gastrointestinal disorders (eosinophilic esophagitis, eosinophilic gastritis, eosinophilic gastroenteritis, or eosinophilic colitis), a (food) allergy, or atopic dermatitis.

Thus, an "an above-normal number of granulocyte in a tissue" defines that the number of eosinophils or mast cells is raised in a subject suffering from one of those disorders compared to a healthy individual. If the tissue of a healthy person contains no granulocytes normally, "an above-normal number of eosinophils in a tissue" is at least 1, 10, 100 eosinophils in an high power field (HPF) or 400× on a microscopic histologic tissue or lavage of a tissue on a slide.

If the tissue of a healthy person contains granulocytes normally, "an above-normal number of granulocytes in a tissue" means an increase of at least 10%, 25%, 50%, 100%, 500%, or 1000% compared to the number of granulocytes found in the same tissue of an healthy individual.

DETAILED DESCRIPTION OF THE INVENTION

The section headings serve to clarify the subject matter and should not be interpreted to limit the subject matter. If ranges of values are disclosed each individual value is considered to be covered by the range, in particular, each integer number. If not noted otherwise, values in % relate to weight/weight (w/w) values. It has been surprisingly found that the combination of cocoa polyphenols with soluble dietary fibers is useful in decreasing the amount of eosinophils. This finding was made in a mice model for eosinophilic esophagitis. Therefore, it can be concluded that plant phenols can be used in the treatment or prevention of disorders associated with an above-normal number of eosinophils in various tissues (e.g. colon, esophagus, skin, etc.).

Compositions

The compositions of the invention comprise at least two ingredients, plant polyphenols and soluble dietary fiber. Without being bound to any theory we presume that the (plant) polyphenols as found in a cocoa extract represent the active ingredients (cocoa polyphenols). Thus, the invention relates to compositions comprising plant polyphenols, in particular, plant polyphenols as found in cocoa extract, and fermentable and/or soluble dietary fiber. Fermentable dietary fiber lead to production of short chain fatty acid (SOFA) by the microbiota that are exert anti-inflammatory effect systematically.

The preferred polyphenol is at least one procyanidin. Procyanidin can be comprised in cocoa extracts or concentrates. In particular, the composition of the invention can comprise cocoa extracts or concentrates which in turn comprise polyphenols comprising at least one procyanidin. In a particular embodiment, the composition comprises polyphenols comprising at least one procyanidin and other polyphenols. In a further preferred embodiment, the polyphenols are present at a concentration in the extracts or concentrates or/and ratio that can be found in cocoa extracts or concentrates.

Plant Polyphenols

The composition comprises at least one plant polyphenol. Plant polyphenols comprise at least 2, 3, 4, 5, or 6 phenolic residues. Particularly preferred are plant phenols comprising 2 phenolic residues. The plant phenols preferentially do merely consist of hydrogen, carbon, and oxygen. The plant phenols preferentially do comprise or consist of a residue selected from the group consisting of at least one cyclohexan residue, phenolic residue, H— residue, OH— residue, C= residue, $CO_2H$— residue, ethyl residue, or —O— residue.

The composition can comprise at least one, at least two, at least three, or at least four different plant polyphenols. It can be expected that a combination of plant polyphenols with dietary fiber will show synergistic effects on a disorder associated with an above-normal number of eosinophils in a tissue. The phenols are phenols that occur in natural plant sources. The natural sources can be cocoa (or grape). The phenols may be extracted from those natural sources by any known extraction technique, like an extraction with water or an organic solvent, like ethanol or ether.

The compositions comprise "Procyanidin." In particular the composition can comprise procyanidin B1 (cis,trans"-4, 8"-Bi-(3,3',4',5,7-Pentahydroxyflavane)), procyanidin B2 (4,8"-Bi-[(+)-epicatech in], cis,cis"-4,8"-Bi(3,3',4',5,7-pentahydroxyflavane)), other procyanidins not being either procyanidin B1 or B2. In particular, the composition can comprise multimers of said procyanidins. Particular preferred are 2 to 20 mers, 5 to 15 mers, or 7 to 10 mers. The composition can comprise at least one procyanidin B1 or/and one or more multimers thereof.

The composition can comprise at least one procyanidin B2 or/and one or more multimers thereof.

The composition can comprise at least one procyanidin not being procyanidin B1 or B2 B1 or/and one or more multimers thereof.

The composition can comprise at least one procyanidin B1 and at least procyanidin B2 or/and one or more multimers of procyanidin B1 and procyanidin B2.

The composition can comprise at least one procyanidin B1 or/and one or more multimers thereof; and at least one procyanidin not being procyanidin B1 or B2 B1 or/and one or more multimers thereof.

The composition can comprise at least one procyanidin B2 or/and one or more multimers thereof; and at least one procyanidin not being procyanidin B1 or B2 B1 or/and one or more multimers thereof.

The composition can comprise at least one procyanidin B1 or/and one or more multimers thereof; and at least one procyanidin B2 or/and one or more multimers thereof; and at least one procyanidin not being procyanidin B1 or B2 B1 or/and one or more multimers thereof.

It is also contemplated to include further polyphenols which are not procyanidins into the composition.

Mixtures of these plant phenols are also contemplated. In particular, the mixture can comprise at least 1, 2, 3, 4, 5, 6, 7, 8, 9, 10, 11, 12 of the above described polyphenols. The composition can comprise any permutation of the above described phenols in the composition.

In a particular embodiment epicatechin is included in the composition.

Epicatechin can be included into the composition at an amount of 0.1% to 5%, 0.5% to 1.5%, or 0.75% to 1.25% (w/w) of the composition.

In a preferred embodiment, the compositions comprising polyphenols comprising procyanidin and/epicatechin for use in the treatment or prevention of eosinophilic esophagitis are obtained from cocoa and are thus cocoa polyphenol extracts.

The total amount of polyphenols in the extract or concentrate can be between 20% and 60%, between 30% and 55%, or between 40% and 50%, by weight.

The extracts or concentrates can comprise 0.01% to 5%, or 0.1% to 0.5%, or 0.5% to 0.15% by weight procyanidin B1 or multimers of said procyanidin.

In a preferred embodiment, the extracts or concentrates comprise 1% to 0.0%, or 2% to 7%, or 3% to 5% by weight procyanidin B2 or multimers of said procyanidin.

In a preferred embodiment, the extracts or concentrates comprise 0.5% to 10%, or 1% to 5%, or 1.5% to 2% by weight of other procyanidins not being either procyanidin B1 or B2 or multimers of said procyanidins.

The extracts or concentrates can be diluted for use in a composition in the prevention or treatment of eosinophilic esophagitis.

In some embodiments the composition may comprise the extracts or concentrates in an amount of about 1% to 20%, 2% to 15%, 3% to 10%, or 5% to 7% by weight based on the weight of the composition.

In a preferred embodiment, the composition for use in the prevention or treatment of EGID comprises 0.01% to 0.5%, or 0.02% to 0.1%, or 0.04% to 0.07% by weight procyanidin B1 or multimers of said procyanidin.

In a preferred embodiment, the composition comprises 0.01% to 1.0%, or 0.1% to 0.9%, or 0.2% to 0.3% be weight procyanidin B2 or multimers of said procyanidin.

In a preferred embodiment, the composition comprises 0.5% to 10%, or 1% to 5%, or 1.5% to 2% by weight of other procyanidins not being either procyanidin B1 or B2 or multimers of said procyanidins.

Particular preferred are 2 to 20 mers, 5 to 15 mers, or 7 to 10 mers of procyanidin B1, procyanidin B2, or other procyanidins not being either procyanidin B1 or B2.

Soluble Dietary Fiber

The composition also comprises soluble dietary fiber. A preferred soluble fiber is pectin. It is known that soluble dietary fibers together with probiotic bacteria promote several beneficial health effects, including the production of short-chain fatty acids which in turn can have beneficial effects in the organisms. Here it is described that pectin in combination with the compounds found in cocoa extract and other plant extracts (e.g. polyphenols) promotes a synergistic effect on the number of eosinophils in disorders associated with an above-normal number of eosinophils in various tissues.

Without being bound to any theory it is submitted that the beneficial effects for one fermentable and or soluble dietary fiber, pectin, can also be expected for other soluble dietary fibers. Therefore, it is plausible that all fibers exerting a positive effect on the gut flora, the effect, for example, being the raised production of short-chain fatty acids, will display the observed synergistic effect. Thus, the invention is directed to soluble dietary fibers, in particular, fermetable and or soluble dietary fiber capable of raising the production of at least one short-chain fatty acid in the gut of an animal. The at least one short-chain fatty acid is selected from the group consisting of formic acid, acetic acid, propionic acid, isobutyric acid (2-methylpropanoic acid), butyric acid, isovaleric acid (3-methylbutanoic acid), valeric acid (pentanoic acid), or combinations thereof. The soluble dietary fiber can alternatively raise the production of at least 2, 3, 4, 5, 6, or all 7 of the short-chain fatty acids.

Soluble dietary fibers in the sense of the invention are pectin, alginic acids, fructans like inulin, fructo- or galacto-oligosaccharides, raffinose, xylose, polydextrose, lactulose, Acacia gum, Guarm Gum including Partially Hydrolyzed Guar Gum (PHGG), milk-derived oligosaccharides, partially hydrolyzed fibers or a combination thereof.

Formulations

The above described compositions can be formulated in liquid or solid form. The liquid form can be formulated to be in a form suitable for spraying, that is, in the form of a spray. This can be achieved by connecting a compartment containing the composition to a spray nozzle. The liquid when transported through the spray nozzle is atomized allowing the obtained droplets to distribute evenly onto a surface. Various ways to transport a liquid through a spray nozzle are known to the skilled person. For example, the container containing the composition may be under pressure compared to the surrounding atmospheric air pressure. Alternatively, a pump mechanism may transport the spray through the nozzle. The use of a spray allows, for example, to spray the composition via the oral cavity into the esophagus and thereby bring the composition into direct contact with the esophageal mucosa. Subsequently, the composition can be absorbed by the mucosa and then achieve a systemical distribution within the body.

The compositions can further comprise at least one additional active agent, carrier, vehicle, excipient, or auxiliary agent identifiable by a person skilled in the art upon reading of the present disclosure.

The composition can be in the form of an oral nutritional supplement, a nutritional composition or pharmaceutical product. A nutritional composition, oral nutritional supplement or pharmaceutical product can comprise the composition or kit of the invention.

Nutritional Composition

As used herein, the term "nutritional composition" includes, but is not limited to, complete nutritional compositions, partial or incomplete nutritional compositions, and disease or condition specific nutritional compositions. A complete nutritional composition (i.e., those which contain all the essential macro and micro nutrients) can be used as a sole source of nutrition for the patient or as an oral nutritional supplement (ONS). Patients can receive 100% of their nutritional requirements from such complete nutritional composition. A partial or incomplete nutritional composition does not contain all the essential macro and micro nutrients and cannot be used as a sole source of nutrition for the patient. Partial or incomplete nutritional compositions can be used as a nutritional supplement. An oral supplemental nutritional (ONS) composition may provide partial or complete nutritional composition or can contain mainly or exclusively the essential active ingredients of the claimed composition (the plant phenols) and can be consumed in addition to the regular nutrition of a patient.

A disease or condition specific nutritional composition is a composition that delivers nutrients or pharmaceuticals and can be a complete or partial nutritional composition.

A complete nutritional composition has an energy density of having a caloric density of 0.5-3 kcal/ml (2.0-10.5 kJ/ml).

A nutritional composition may additionally comprise the following nutrients and micronutrients: a source of proteins, a source of lipids, a source of carbohydrates, vitamins or minerals. A complete nutritional composition comprises a source of proteins, a source of lipids, a source of carbohydrates, vitamins and minerals.

A complete nutritional composition comprises 10-40 en % protein, 10-60 en % carbohydrates, and 20-80 en % fat. "en %" is the amount of energy provided to the total of the energy of the nutritional composition.

The composition may also contain anti-oxidants, stabilizers (when provided in solid form) or emulsifiers (when provided in liquid form).

Source of Proteins

The source of protein is chosen as to complement or enhance the effects of the composition on the number eosinophils. Thus, the sources of protein should be hypoallergenic, or less allergenic then milk.

Accordingly, the source of proteins is a known hypoallergenic/low allergenic source of protein and can consist of free amino acids, intact protein, in particular, a hypo-allergic protein, protein hydrolysates, preferably extensively hydrolyzed proteins, or combinations thereof. Useful hypo-allergenic proteins are plant proteins. Thus, the composition can be an amino acid-based formula, this means, the only source of amino acids are free amino acids, a plant protein based formula, this means, the proteins in the composition are plant proteins, or a hydrolyzed protein based formula, that means, the proteins in the composition are all (extensively) hydrolyzed, not intact proteins.

The composition comprises non-dispensable, semi-dispensable, and dispensable amino acids in free or bound form.

Each amino acid is present in an amount of 0.5%-25% of the total amino acids independent thereof whether the amino acid is present in free or bound form.

Amino Acids as Source of Protein

Thus, in another embodiment, the nutritional composition further includes one or more free amino acids. Non-limiting examples of amino acids include alanine, arginine, asparagine, aspartate, citrulline, cysteine, glutamate, glutamine, glycine, histidine, hydroxyproline, hydroxyserine, hydroxytyrosine, hydroxylysine, isoleucine, leucine, lysine, methionine, phenylalanine, proline, serine, taurine, threonine, tryptophan, tyrosine, valine. Examples for non protein amino acids are citrulline, HICA (Alpha-Hydroxyisocaproic Acid), HIVA (Alpha-Hydroxyisovaleric Acid), HIMVA (alpha-hydroxymethylvaleric acid) or a combination thereof.

Free amino acids can be the only source of protein in the composition or combined with other sources of protein. Each amino acid is present in an amount of 0.5%-25% of the total amino acids.

Plant Proteins as Source of Protein

A preferred source of protein is plant protein because many plant proteins are hypo-allergenic. Plant proteins as intact proteins have advantages over the use of hydrolyzed protein or amino acids in free form because they superior in the nutritional composition with respect to taste and texture. Thus, plant proteins display an organoleptic superiority. Organoleptic superiority is especially important to ensure compliance with the dietary treatment of older children and teens which is rather low with compositions comprising hydrolyzed protein or amino acids in free form. A further advantage is the lower cost compared to nutritional compositions comprising hydrolyzed protein or amino acids in free form. A yet further advantage is that they appear to the consumer as a more normal diet.

Thus, the source of protein can be a plant protein selected from the group consisting of potato protein, rice protein, legumes proteins (such as but not limited to pea, chickpea, beans), non-legumes proteins (vegetables), as well as millet, quinoa, lupin, canola, tapioca or a combination thereof.

Potato protein can be a protein potato isolate (e.g. PROGO, Solanic, NL).

Rice protein can be a white or brown rice protein.

Plant proteins can be the only source of protein in the composition or combined with other sources of protein, in particular, to supplement it with amino acids that are not present or underrepresented in plant protein to provide the required amounts of amino acids required by an animal or human. Proteins can be in intact, partially hydrolyzed, extensively hydrolyzed, cooked or modified in any other form to reduce allergenicity Hydrolysed Protein as Source of Protein The source of protein can be hydrolysed protein, preferably extensively hydrolysed protein. Hydrolysis leads to smaller peptide fragments and eventually amino acids thereby removing potentially allergenic acting epitopes. Suitable proteins for hydrolysis are plant, animal and milk proteins. Preferred partial or extensively hydrolyzed proteins are milk proteins. Milk proteins can be casein or whey proteins. Hydrolyzed proteins can be the only source of protein in the composition or combined with other sources of protein.

Source of Fats

The present nutritional composition can further comprise fat.

The fat may either be an animal fat or a vegetable fat or both. Although animal fats such have essentially equal caloric and nutritional values and can be used interchangeably, vegetable oils are preferred in the practice of the present invention due to their readily availability, ease of formulation, and lower concentration of saturated fatty acids. Fat sources to be used comprise fish oil, algal oil, corn oil, sunflower oil, safflower oil, canola oil, olive oil, high-oleic sunflower oil, high-oleic safflower oil, peanuts oil, grape-oil, palm-derived oils, avocado oils, almond oil, fish oil, coconut oil and/or soybean oil or combinations thereof. In one embodiment the fat blend will provide an optimal ratio of linoleic (LA) to alpha-linolenic acid (ALA). Preferably the level of LA provided is between 2-80% wt of the total fat content. Preferably the level of ALA provided is between 0.5% to 25% wt of the total fat content.

The fat may include medium chain triglycerides (MCT, preferably 8 to 10 carbon atoms long, but could also include 12 and 14 carbons as well including the branched-chain isomers and even- and odd-numbered carbons fatty acids), long chain triglycerides (LCT, and their branched-chain isomers) or any combination of the two types. MCTs are beneficial because they are easily absorbed and metabolized in a metabolically-stressed patient especially because they serve as alternative fuel substrate and as bioactive and as a source for ketone bodies. Moreover, the use of MCTs will reduce the risk of nutrient malabsorption. LCT sources, such as canola oil, or any oil from the listed above, such as rapeseed oil, or corn oil are preferred because they can reduce immune suppression associated with certain types of fatty acids concentrated in the body.

For increased anti-inflammatory effect the fat blend preferably comprises eicosapentanoic acid and docosahexanoic acid. Marine oils containing DHA are preferably present in the composition according to the invention in an amount lower than or equal to 25 weight %, based on total fat. On the other hand, inclusion of eicosapentanoic acid (EPA) is highly desirable for obtaining the maximum health effect. In an embodiment, the amount of EPA ranges preferably between 4 weight % and 15 weight %, more preferably between 8 weight % and 13 weight % based on total fatty acids.

It is also preferred to include branched chain fatty acids (BCFA) into the composition. In BCFAs often the fatty acyl chain is saturated and the branch is a methyl-group. They are known to be important for the efficient functioning of the human gut and are a family of saturated fatty acids found in specific locations, such as the skin sebaceous gland and the moll's gland of the eye. BCFAs are thought to play an important role in maintaining membrane fluidity under oxidative conditions. BCFAs can form a protective biofilm on the lumen of the digestive tract, providing a unique niche that fosters the development of a healthy gut microbiota and positively interact with the other components of the composition.

The liquid nutritional composition according to the invention may beneficially comprise an emulsifier. Commonly known emulsifiers may be used and generally the emulsifier contributes to the energy content of the fat in said composition.

Minerals

In a further embodiment the nutritional composition may comprise minerals such as boron, calcium, calcium acetate, calcium gluconate, calcium chloride, calcium lactate, calcium phosphate, calcium sulfate, chloride, chromium, chromium chloride, chromium picolonate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters and chelates of any mineral compound cited above.

The are included in amounts to meet the daily requirements as defined by the FDA.

Vitamins

In a further embodiment the nutritional composition comprises further vitamins such as vitamin B1 (thiamin, thiamin pyrophosphate, TPP, thiamin triphosphate, TTP, thiamin hydrochloride, thiamin mononitrate), vitamin B2 (riboflavin, flavin mononucleotide, FMN, flavin adenine dinucleotide, FAD, lactoflavin, ovoflavin), vitamin B3 (niacin, nicotinic acid, nicotinamide, niacinamide, nicotinamide adenine dinucleotide, NAD, nicotinic acid mononucleotide, NicMN, pyridine-3-carboxylic acid), vitamin B3-precursor tryptophan, vitamin B6 (pyridoxine, pyridoxal, pyridoxamine, pyridoxine hydrochloride), pantothenic acid (pantothenate, panthenol), folate (folic acid, folacin, pteroylglutamic acid), vitamin B12 (cobalamin, methylcobalamin, deoxyadenosylcobalamin, cyanocobalamin, hydroxycobalamin, adenosylcobalamin), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin D3, 1,25,-dihydroxyvitamin D), vitamin E (a-tocopherol, a-tocopherol acetate, a-tocopherol succinate, a-tocopherol nicotinate, a-tocopherol), vitamin K (vitamin K1, phylloquinone, naphthoquinone, vitamin K2, menaquinone-7, vitamin K3, menaquinone-4, menadione, menaquinone-8, menaquinone-8H, menaquinone-9, menaquinone-9H, menaquinone-10, menaquinone-11, menaquinone-12, menaquinone-13), choline, inositol, 6-carotene and any combinations thereof.

The are included in amounts to meet the daily requirements as defined by the FDA.

Format of the Nutritional Composition

In one embodiment, the nutritional composition is selected from the group consisting of an infant feeding composition, a follow-up formula, a growing-up milk, an infant cereal, or a baby nutritional composition. These products are particularly well suited to address and solve the problem of the prevention or reduction of symptoms of disorders like disorders associated with an above-normal number of eosinophils, like eosinophilic esophagitis in babies and young children. However, other products like beverages and powders (sachet format) can also be chosen for older children and adults as described in the following.

In a further embodiment, the nutritional composition is selected from the group consisting of a beverage product, an amino acid based beverage, a yoghurt product, fermented milk, a fruit juice, a dried powder in sachet format or a cereal bar. These nutritional compositions are well suited for administering plant phenols to older children and adult humans. The nutritional compositions can well be enriched with plant phenols and have a credible image to provide a health oriented functional nutritional composition to the consumers.

A particular need for products to reduce symptoms of eosinophilic esophagitis may be in the clinical environment, such as in hospitals, clinics and homes for elderly persons. Therefore, in a still further embodiment, the nutritional composition is a food for specific medical purposes such as a health care nutritional composition for oral feeding, and/or a nutritional product for enteral or parental feeding. In the latter case it will only include ingredients which are suitable for parenteral feeding. Ingredients that are suitable for parental feeding are known to the person skilled in the art. In particular, a parental feeding composition will contain the plant phenols and the soluble dietary fiber in pure or substantially pure form (i.e. usually not be provided in the form of plant extracts which are only enriched for the plant phenol) but the composition can also comprise other ingredients that are known to be suitable for parenteral nutrition. A further advantage of the invention is that plant phenol can be provided in relatively high local concentration and low volumes of a medical nutritional composition and hence be administered effectively to patients in such need.

Viscosity

If the nutritional composition is a liquid it has a viscosity below 150 mPa·s, preferably below 100 mPa·s, more preferably below 80 mPa·s, even more preferably below 70 mPa·s. The viscosity is determined in a rotational rheometer using a cone-plate geometry at 20° C. at a shear rate of 50 1/s.

If the composition is provided as texturised product (pudding etc.) ready for consumption to be eaten with a spoon a viscosity of at least 350 mPa·s, preferably above 750 mPa·s, more preferably between 1000 and 4000 mPa·s. is preferred.

Kits

The above compositions may also be provided as kits. In those kits the all or a part of the ingredients of the above described compositions are provided in a separate (i.e. not mixed) form. A kit of the invention can comprise the plant phenols on the one hand, and all the remaining ingredients (the soluble dietary fiber and others) on the other hand in separate form. A kit of the invention can comprise at least two or three plant phenols provided in a separate form. In an alternative embodiment, the kits can comprise each of the ingredients of the above described composition in a separate form.

Therapeutical Uses and Methods

The composition or the kit of the invention can be used in the treatment or prevention of disorders or methods for the treatment or prevention of disorders associated with an above-normal number of eosinophils in various tissues. In particular, this relates to the prevention or treatment of an eosinophilic gastrointestinal disorder, allergies, in particular, food allergies, or skin atopic dermatitis.

"Above normal" means more than 10%, 20%, 50%, 100% of the normal number of eosinophils found in the respective tissue.

A treatment results in a reduction of the number of eosinophils, in particular, in the epithelium or mucosa, in particular, in the epithelium of the esophagus.

A reduction in the number of eosinophils is defined as the reduction of eosinophils that are found in a high power field of a microscope in a mucosal biopsy of the esophagus below a value of 10-20, particularly 15 in human being that is suffering from eosinophilic esophagitis. Thus, a reduction in the sense of the invention is a significant reduction compared to a positive control in animal models. A reduction in the sense of the invention can be a reduction to values below 19, 18, 17, 16, 15, 14, 13, 12, 11, 10, 9, 8, 7, 6, 5, 4, 3, 2, 1 or to 0 in a high power field of a microscope in a biopsy of a tissue, in particular, a mucosal biopsy of the human esophagus. Alternatively the reduction can be defined by reference to the number of eosinophils a subject with an above-normal number of eosinophils in a tissue, e.g. suffering from eosinophilic esophagitis has or is expected to have if no preventive measures are taken using the composition of the invention. Thus, a reduction may be a percentage of reduction (of at least 50%, 60%, 70%, 80%, 90%, 95%, 99%, or 100%) in reference to a number of eosinophils found in a high power field of a microscope in a biopsy of the respective tissue, e.g. mucosal biopsy of the esophagus of an animal or human being that is suffering from eosinophilic esophagitis. Alternatively, a reduction in the sense of the invention may be a reduction in absolute numbers by 5, 6, 7, 8, 9, 10, 11, 12, 13, 14, 15, 16, 17, 18, 19, or 20 or more than 20 in reference to a number of eosinophils found in a high power field of a microscope in a mucosal biopsy of the esophagus of a human being that is suffering from eosinophilic esophagitis. The reference value can be in the range of 10-20, or be 15. The reduction may be observed after 5, 10, 15, 20, 25, 30, 60, 120 days of treatment.

The compositions and kits can be provided in a form that is suitable for oral or topical administration and then be administered accordingly. Administration can start before the symptoms occur in a subject, concurrently together with the appearance of the symptoms or after the symptoms have shown. Administration can be performed for 1, 20, 30, 60, 120, 360 days or longer. If the subject is a human, the subject to which the composition is administered, can be between the age of 4 months and 6 years, between the age of 6 years and 18 years, or be an adult person.

In an embodiment, the composition is intended for consumption by an animal, preferably a cat or a dog. Similarly as with humans, eosinophilic esophagitis can be observed in animals, in particular with domesticated animals and animals kept as pets. Advantageously, the current invention provides a liquid which can be provided to a companion animal by his owner.

The sum of plant phenols in the composition to be administered to a human being is an amount preferably in the range from 3 mg/kg body weight per day to 100 mg/kg body weight per day, preferably 10 to 50 mg/kg body weight day. Preferably, the composition provides from about 25 mg to 10 g per day, from 50 mg to 10 g per day, preferably from 100 mg to 5 g per day, even more preferably from 300 mg to 1 g per day.

The sum of the soluble dietary fiber in the composition to be administered to a human being is an amount preferably equally to deliver 1-40 g/day if given as a sole source nutrition or 0.25-10 g/serving if given as partial feeding.

These preferred doses allow to provide on the one hand sufficient plant phenols and soluble dietary fiber to a relevant patient per day in order to provide the expected health benefit and on the other hand not to overdose plant phenols and fiber to prevent the risk of any potential undesirable or toxic effects to the patient.

Methods of Production

A method for producing the above described composition is provided and comprises providing at least one of the above described plant phenols, adding the soluble dietary fiber, and adding optionally at least one further ingredient, for example, selected from the group consisting of one or more amino acids, fat, or carbohydrate, adding optionally at least one nutrient or micronutrient, adding a carrier or/and water.

Those skilled in the art will understand that they can freely combine all features of the present invention disclosed herein. In particular, features described for different embodiments of the present invention may be combined. Further advantages and features of the present invention are apparent from the figures and examples.

EXAMPLES

Example 1: Effect of Polyphenols on the Eosinophil Count 5-8 weeks old female Balb/c mice were sensitized by epicutaneous application of 200 µg of an allergic extract. A small part of the back of the mouse was shaved. A patch of sterile gauze (1×1 cm) with the allergen was secured to the skin with a bio-occlusive transparent dressing 2461 (Johnson and Johnson) and a Band-Aid. The patch remained on the skin for a sensitization period of 7 consecutive days till it felt or was removed at day 8 (day 8 to day 15). The mice were exposed on day 36 to an intranasal challenge (100 µg) in anesthetized mice and mice were harvested on day 38.

*Aspergillus fumigatus* antigen extract was obtained from Greer Laboratories, Lenoir, N.C. and were diluted to 2 mg/mL with normal saline (designated as A.f.).

Intranasal allergen exposure was performed with 100 µg of A.f. in a total volume of 50 µl (25 µl per nostril).

Effect of cocoa polyphenols and soluble dietary fibers was tested using a plant phenols extract in the food from cocoa extract.

The diets were as follows:

|  | Base diet | Amount of soluble dietary fiber in respective diet (w/w) | Amount of cocoa polyphenols in respective diet |
|---|---|---|---|
| Regular diet | Kliba NAFAG diet 3437 | 4.5% | — |
| Low fiber diet | Kliba NAFAG diet 2122 | 0.6% | — |
| High fiber diet | Kliba NAFAG diet 3437 | 30% citrus pectin Classic CU 201 | — |
| Regular diet, 6% cocoa extract | Kliba NAFAG diet 2122 | 4.5% | 6% cocoa extract (comprising 45% polyphenols) purchased from Monteloeder (Spain) |
| High fiber diet, 6% cocoa extract | Kliba NAFAG diet 3437 | 30% citrus pectin Classic CU 201 | 6% cocoa extract (comprising 45% polyphenols) purchased from Monteloeder (Spain) |

The mice were treated according to the protocol contained in the following table:

|  | Number of mice | Epicutaneous sensitization | Challenges | Treatment |
|---|---|---|---|---|
| Group A | 8 | 2X saline | 1x A.f. | Regular diet D0 to D38 |
| Group B | 8 | 2X A.f. | 1x A.f. | Regular diet D0 to D38 |
| Group C | 8 | 2X A.f. | 1x A.f. | Low fiber diet D0 to D38 |
| Group D | 8 | 2X A.f. | 1X A.f. | High fiber diet D0 to D38 |
| Group E | 8 | 2X A.f. | 1X A.f. | Regular Diet D0 to D38 6% cocoa extract D28 to D38 |
| Group F | 8 | 2X A.f. | 1X A.f. | High fiber diet D0 to D28 High fiber diet 6% cocoa extract D28 to D38 |

Figure 1:
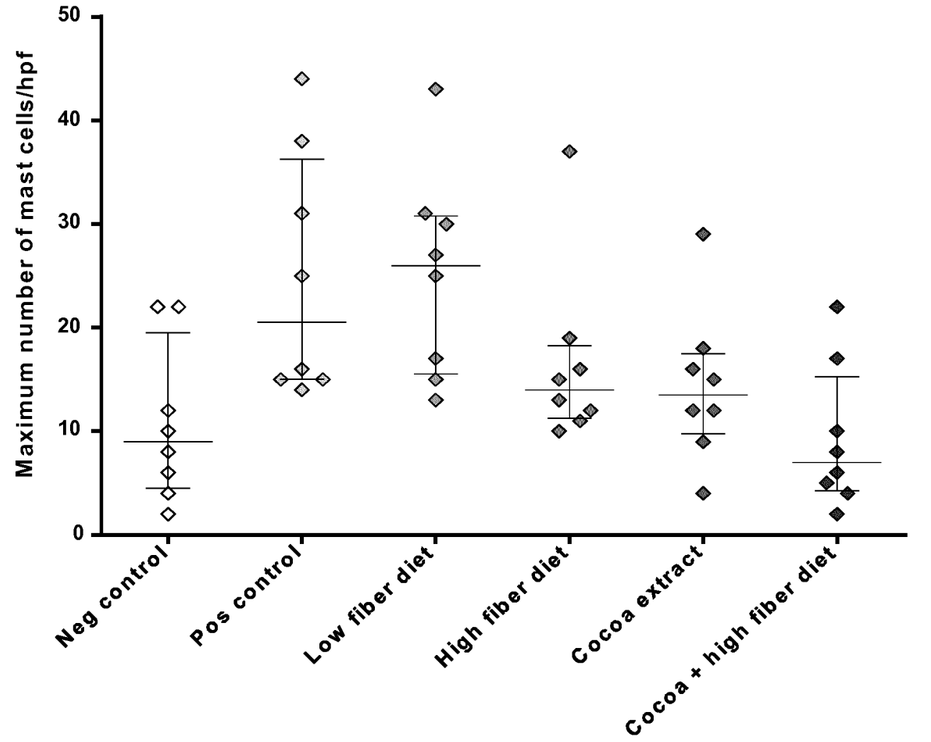
FIG. 1. Effects of compositions comprising low fiber, high fiber, a cocoa extract, and the combination of cocoa extract combined with the high fiber diet on the mast cell number (Mast cells in Jejunum) in response to a challenge and optionally sensitization with an *Aspergillus fumigatus* extract.

As can be seen from FIG. 1 the low fiber diet did not result in a reduction of mast cells number. Both the high fiber and low fiber/cocoa extract effected as substantial reduction of eosinophil number. Surprisingly, the combined administration of high fiber and cocoa extract resulted in an even more drastic reduction of the number of mast cells.

Example 2: Clinical Trial

Seven cohorts of 20-30 subjects in the age of 1-60 years old suffering from EGID as indicated by the presence of more than 15 eosinophils per high power field in a mucosal biopsy obtained during esophagogastroduodenoscopy receive an amino acid based composition VIVONEX®

PEDIATRIC, Alfamino or plant protein based formula further containing extracts as indicated in the table below.

At standard dilution, VIVONEX® PEDIATRIC is a 0.8 kcal/ml formula having by % of kcal:12% protein (free amino acids); 63% carbohydrate and 25% fat. A MCT:LCT Ratio of 70:30; n6:n3 Ratio of 7.7:1; Osmolality (mOsm/kg water) of 360; free water of 89%; it meets or exceeds 100% DRIs for protein and 25 key vitamins and minerals; supplemental Glutamine: 3.0 g/L; Supplemental L-Arginine:

2.0 g/L. The plant protein formula may in include the macronutrients distribution as describe above: 0.5-3 kcal/ml, 10-40 en % protein, 10-60 en % carbohydrates, and 20-80 en % fat.

The composition for group B contains cocoa extracts contains 6% of polylphenols (prepared from Cocoa extract 45% polyphenols from Monteloeder, Spain). This cocoa extract from Monteloeder contains 1.0% Catechin, 9.0% Epicatechin, 1.0% Procyanidin B1, 4.0% Procyanidin B2, 30% of 1 to 10-mers of other procyanidins). The composition for group C comprises 30% citrus pectin Classic CU 201, Herbstreith. The composition for group D comprises both the cocoa extract and the citrus pectin at the amounts indicated above.

|         | Number of subjects | Agent(s)                    |
|---------|--------------------|-----------------------------|
| Group A | 15                 | Water                       |
| Group B | 15                 | 6% cocoa extract            |
| Group C | 15                 | 30% pectin                  |
| Group D | 15                 | 6% cocoa extract 30% pectin |

The subjects receive the extracts in such an amount that 500 mg of the respective polyphenol(s) are administered daily. The number of eosinophils is determined as the number of eosinophils visible in the high power field of a mucosal biopsy obtained during esophagogastroduodenoscopy at day 15 and 30 after start of the study. Known associated symptoms like swallowing difficulty, food impaction, and heartburn are also observed in the study.

The invention claimed is:

1. A method of prevention or treatment of at least one disorder selected from the group consisting of eosinophilic gastritis, eosinophilic enterocolitis and eosinophilic colitis, the method comprising administering a composition comprising at least one cocoa polyphenol and at least one fermentable dietary fiber to an individual in need of same.

2. The method according to claim 1, wherein the at least one fermentable dietary fiber is pectin.

3. The method according to claim 2, wherein the composition comprises 1 to 20% (w/w) of a plant extract or plant concentrate, wherein the at least one cocoa polyphenol is between 20 and 60% (w/w) of the plant extract or plant concentrate.

4. The method according to claim 1, wherein the composition further comprises a source of protein.

5. The method according to claim 4, wherein the protein is selected from the group consisting of potato protein, rice protein, legume proteins, millet, quinoa, lupin, canola, tapioca, and combinations thereof.

6. The method according to claim 1, wherein the composition comprises a procyanidin selected from the group consisting of procyanidin B1, procyanidin B2, a procyanidin not being procyanidin B1 or B2, one or more multimers of procyanidin B1, procyanidin B2 or the procyanidins not being B1 or B2, the multimer being any of a 2-mer to a 10-mer; and combinations thereof.

7. The method according to claim 1, wherein the composition comprises 0.01% to 0.5% (w/w) procyanidin B1 or multimers of the procyanidin.

8. The method according to claim 1, wherein the composition comprises 0.01% to 1.0% (w/w) procyanidin B2 or multimers of the procyanidin.

9. The method according to claim 1, wherein the composition comprises 0.5% to 10% (w/w) of procyanidins not being either procyanidin B1 or B2 or multimers of the procyanidins.

10. The method according to claim 1, wherein the composition comprises 0.01% to 0.5% (w/w) epicatechin.

11. The method according to claim 1, wherein the at least one cocoa polyphenol is comprised in a plant extract or a plant concentrate.

12. The method according to claim 1, wherein the composition is administered orally, topical-orally, or in the form of a spray.

13. The method according to claim 1, wherein the individual is a human or a pet animal.

14. The method according to claim 1, wherein the composition is in a form selected from the group consisting of a nutritional composition, an oral nutritional supplement provided as sole source of nutrition or as partial nutrition, complete or incomplete nutrition and a pharmaceutical product.

15. The method according to claim 1, wherein the composition has a caloric density of 0.5-3.0 kcal/ml.

16. The method according to claim 1, wherein the composition comprises 10-40 en % protein, 10-60 en % carbohydrates, and 20-80 en % fat.

17. The method according to claim 16, wherein the fat is selected from the group consisting of fish oil, vegetable oil, medium chain triglycerides which are 8 to 14 carbon atoms long, and mixtures thereof.

18. The method according to claim 1, wherein the composition comprises fat, and 0-70 wt. % of the fat are medium chain triglycerides which are 8 to 14 carbon atoms long.

19. The method according to claim 1, wherein the composition comprises carbohydrates selected from the group consisting of maltodextrin, starch, lactose, modified carbohydrates, sugar alcohols, and combinations thereof.

20. The method according to claim 1, wherein the at least one fermentable dietary fiber is 25 wt. % to 35 wt. % of the composition.

21. The method according to claim 1, wherein the at least one fermentable dietary fiber is selected from the group consisting of pectin, hydrolyzed pectin, beta-glucan, inulin, fructo-oligosaccharides, galacto-oligosaccharides, alginic acids, raffinose, xylose, polydextrose, lactulose, Acacia gum, Guar Gum, and milk-derived oligosaccharides, wherein the composition comprises 2 to 80% (w/w) of the at least one fermentable dietary fiber.

22. The method according to claim 1, wherein the method is for prevention or treatment of at least one disorder selected from the group consisting of eosinophilic enterocolitis and eosinophilic colitis.

23. The method according to claim 1, wherein the method is for prevention or treatment of at least one disorder selected from the group consisting of eosinophilic enterocolitis and eosinophilic colitis, wherein the at least one fermentable dietary fiber is selected from the group consisting of pectin, hydrolyzed pectin, beta-glucan, inulin, fructo-oligosaccharides, galacto-oligosaccharides, alginic acids, raffinose, xylose, polydextrose, lactulose, Acacia gum, Guar Gum, and milk-derived oligosaccharides,
   wherein the composition comprises 2 to 80% (w/w) of the at least one fermentable dietary fiber.

\* \* \* \* \*